United States Patent [19]

Rajamannan

[11] Patent Number: 5,260,341
[45] Date of Patent: Nov. 9, 1993

[54] PRODUCT AND PROCESS FOR TREATING BOVINE MASTITIS AND BOVINE METRITIS

[75] Inventor: A. H. J. Rajamannan, Minneapolis, Minn.

[73] Assignee: Agro-K Corporation Inc., Minneapolis, Minn.

[21] Appl. No.: 913,034

[22] Filed: Jul. 14, 1992

[51] Int. Cl.$^5$ .................... A61K 31/12; A61K 31/56; A61K 35/00; A61K 35/78

[52] U.S. Cl. .................... 514/675; 514/169; 514/886; 424/115; 424/195.1

[58] Field of Search ............... 514/675, 169, 886, 887; 424/195.1, 115

[56] References Cited

U.S. PATENT DOCUMENTS 4,320,149 3/1982 Engel et al. .................... 514/675

Primary Examiner—John W. Rollins
Attorney, Agent, or Firm—Herman H. Bains

[57] ABSTRACT

A product for treating bovine mastitis and bovine metritis includes mixture of diacetyl and acetoin. The diacetyl and acetoin is produced by fermentation of milk and is then distilled and concentrated. The concentrated mixture of diacetyl and acetoin is infused into the udder cistern of a cow when treating mastitis, and is infused into the uterus of a cow when treating metritis.

10 Claims, No Drawings

PRODUCT AND PROCESS FOR TREATING BOVINE MASTITIS AND BOVINE METRITIS

FIELD OF THE INVENTION

This invention relates to a product and process for treating bovine mastitis and bovine metritis.

BACKGROUND OF THE INVENTION

Mastitis continues to be a major cause of economic loss in the dairy industry even though there are methods of treating this disease. Currently, the primary method of treating mastitis in cows (inflammation of the udder) as well as treating metritis (inflamation of the uterus) is antibiotic therapy. However, antibiotics thus used tend to leave residues in the milk so that milk from cows treated with antibiotics must be kept from human consumption.

This discarding of the milk from the cows under treatment is one of the more expensive aspects of mastitis. Yet, there are several reasons that milk contaminated with antibiotics should not be sold. Some people are allergic to antibiotics, especially penicillins, and fatalities have occurred relating to allergic reactions. If milk gains a public reputation for containing antibiotics, then sales of liquid milk might decline rapidly. Antibiotics consumed by humans at low dilute levels will allow various pathogenic bacteria that are currently sensitive to these antibiotics to become resistant.

Further, antibiotics can destroy the bacterial cultures used in yogurt and cheese manufacture. Finally, present regulations require milk from treated cows to be kept from the human food chain for three days. New regulations of longer holding times that are envisioned can deal the dairy industry a devasting impact.

SUMMARY OF THE INVENTION

It is an object of this invention to provide an infusible product and process for treating bovine mastitis and bovine metritis. The product is comprised of a mixture of diacetyl and acetoin.

In carrying out the process, the mixture of diacetyl and acetoin is infused into the udder cistern of the infected cow. Similarly, the mixture of diacetyl and acetoin is infused into the uterus of an infected cow when treating metritis. This mixture of diacetyl and acetoin, while having bactericidal characteristics, does not produce the problems associated with antibiotic therapy, namely residual antibiotics in the milk of a treated cow.

DESCRIPTION OF THE PREFERED EMBODIMENT

The present invention is directed to a product and process for effectively treating bovine mastitis and bovine metritis while avoiding the problems of contaminated milk from cows treated with antibiotics. The product used in this treatment comprises a mixture of diacetyl and acetoin which are components of milk fermentation. Milk fermentation using bacteria such as streptococcus diacetilactis, streptococcus lactis, and streptococcus cremoris produce compounds such as diacetyl, acetoin and volatile acids. These end products are of insufficient strength and, when distilled or extracted and concentrated (starter distillate) are used to add flavor to dairy foods. For example, the fermentation end products of diacetyl and acetoin may be concentrated by a factor of five (5×distillate) or a factor of fifteen (15×distillate) in order to acquire the proper concentration. Concentrations by these factors comprise approximately 15 ppm to 50,000 ppm of diacetyl and approximately 2 ppm to 20,000 ppm of acetoin.

Diacetyl is also known as 2,3-butanedione having the formula $CH_3COCOCH_3$. Acetoin is also known as 3-hydroxy 2-butanone, dimethyketol, or acetyl methylcarbinol having the formula $CH_3CHOHCOCH_3$.

This mixture of diacetyl and acetoin may also include an anti-inflammatory agent including cortisone or aloe vera juice. Antibiotics may be added to the mixture for enhancing the efficacy of the diacetyl and acetoin. Such antibiotics may include penicillin, synthetic penicillins (cloxacillin or ampicillin), antibiotic combinations (e.g. penicillin and streptomycin), tetrayclines or neomycins. Tea tree oil (Maleluca) may be added to the mixture to enhance anti-bacterial anti-inflammatory activity in the bovine udder or uterus.

Although mastitis simply means inflammation of the mammary gland, it is clinically understood that the inflammation is caused by some infectious agent, usually bacteria. Mastitic cows usually have a swollen hot udder and show flaky milk on strip test. While there are various species of staphylococcus organisms and streptococcus organisms which cause mastitis in cows, cow-to-cow transmitted mastitis is usually caused by staphylococcus aureus, streptococcus agalactiae, and streptococcus dysgalactiae. On the other hand, environmental mastitis, that is mastitis infection from the environment, is caused primarily by streptococcus uberis and E. coli. Although there are a number of other bacterial organisms that cause bovine mastitis, the organisms referred to above are the most common causes of mastitis.

Experiments using the mixture of diacetyl and acetoin were performed on animals in test trials in the field. The mastitic cows, when diagnosed with hot udder and showing flaky milk on strip test, were classified as to the type of bacterial infection such as E. coli, streptococcus or staphylococcus organisms.

EXAMPLE I

Various concentrations of distilled diacetyl with traces of acetoin and volatile acids in the form of starter distillate were infused into the udder and observations on inflammation reduction, return to normalcy of milk, milk samples for positive bacterial presence, taste test and strip tests were performed.

The following results were obtained:

TABLE I

| Number of Cows | Type of Infection | Strength Diacetyl & Acetoin | Amount of Infusion | 100% Cure |
|---|---|---|---|---|
| 4 | E. Coli | 5 × distillate | 25 cc per treat | 12 hrs |
| 4 | Streptococcus | 5 × distillate | 25 cc per treat | 24–36 hrs |
| 4 | Streptococcus | 15 × distillate | 25 cc per treat | 12 hrs |
| 4 | Staphylococcus | 5 × distillate | 25 cc per treat | 24–42 hrs |
| 4 | Staphylocuccus | 15 × distillate | 25 cc per treat | 18 hrs |

EXAMPLE II

Cows with metritis were randomly divided into antibiotic groups and diacetyl groups.

Cows were infused with the traditional antibiotics or different doses of starter distillate diacetyl. Swabs were taken every 24 hours and uterus was palpated for signs of inflammation. The uterus that did not respond to diacetyl were switched to antibiotics. Results were as follows:

TABLE II

| Number of Cows | Antibiotics | Time Return To Normal | Number of Cows | Diacetyl Acetoin | Return To Normal |
|---|---|---|---|---|---|
| 2 | Normal amounts | 24 hrs | 2 | 100 cc (10×) | 1in48 hrs* |
| 2 | Normal amounts | 48 hrs | 2 | 100 cc (10×) | 72 hrs |
| 2 | Normal amounts | 72 hrs | 2 | 100 cc (10×) 3 times every 12 hours | 48 hrs |

*One switched to antibiotics at end of 48 hours because of infection not cured

These trials show that diacetyl with acetoin can fully replace antibiotics to treat mastitis and most cases of metritis.

Since diacetyl and acetoin are approved for human consumption by the Food and Drug Administration of the United State of America for flavoring Dairy products, the potential contamination of milk of diacetyl post treatment should not be a problem.

What is claimed is:

1. An infusible product for the use in the treatment of bovine mastitis and bovine metritis which is infused into the udder of a cow when treating mastitis or metritis, comprising a concentrated mixture primarily including diacetyl and a trace amount of acetoin which is concentrated by several factors up to a factor of 15.

2. The product as defined in claim 1 wherein said mixture also includes an anti-inflammatory agent selected from the group consisting of cortisone or aloe vera juice.

3. The product as defined in claim 1 wherein said mixture also includes antibiotics for enhancing the efficacy of diacetyl and acetoin.

4. The product as defined in claim 1 wherein said mixture also includes Tea tree oil (Maleluca) for enhancement of antibacterial anti-inflammatory activity in the bovine udder or uterus.

5. The infusible product as defined in claim 1 wherein said mixture of diacetyl and acetoin is concentrated by a factor within the range of 5 to 15.

6. An infusible product for use in the treatment of bovine metritis or bovine mastitis which is infused into the udder of a cow when treating bovine metritis or bovine mastitis, comprising a concentrated mixture including 15 ppm to 50,000 ppm of diacetyl and 2 pm to 20,000 ppm acetoin.

7. A process for the treatment of bovine metritis and bovine metritis comprising the steps of preparing a mixture comprised primarily of diacetyl and a trace amount of acetoin, concentrating the mixture of diacetyl and acetoin by several factors, and infusing the concentrated mixture into the uterus of a cow infected with metritis or mastitis.

8. The process as defined in claim 7 wherein said concentrated mixture also includes an anti-inflammatory agent selected from the group consisting of cortisone and aloe vera juice.

9. The process as defined in claim 7 wherein said concentrated mixture also includes antibiotics.

10. The process as defined in claim 7 wherein said concentrated mixture also includes extracts of Tea tree oil (Maleluca).

* * * * *